Figure 1:
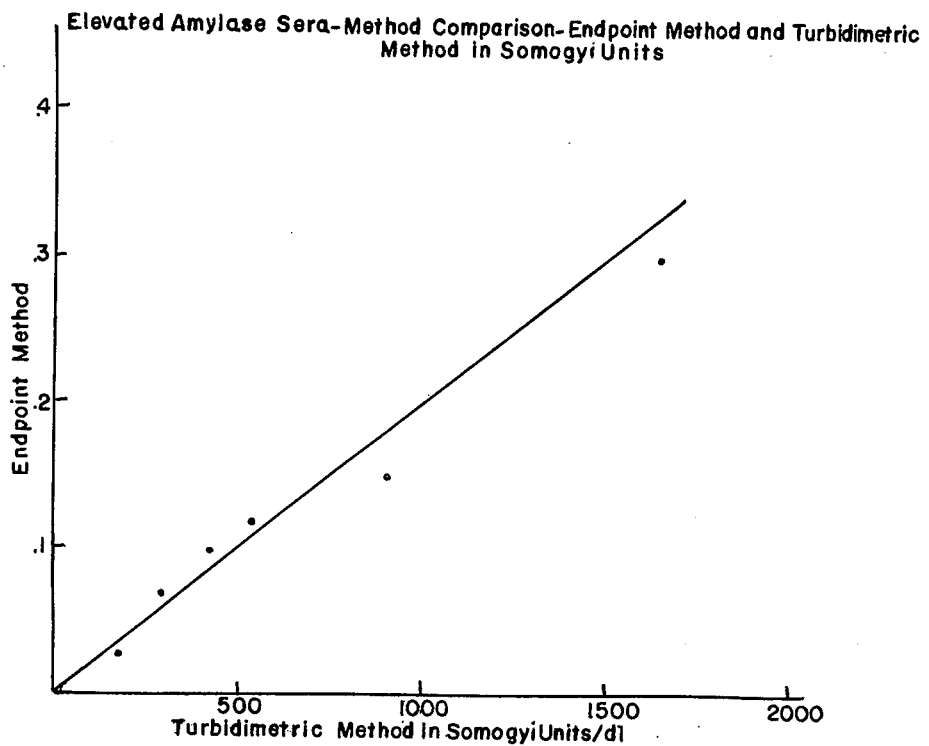
Figure 2:
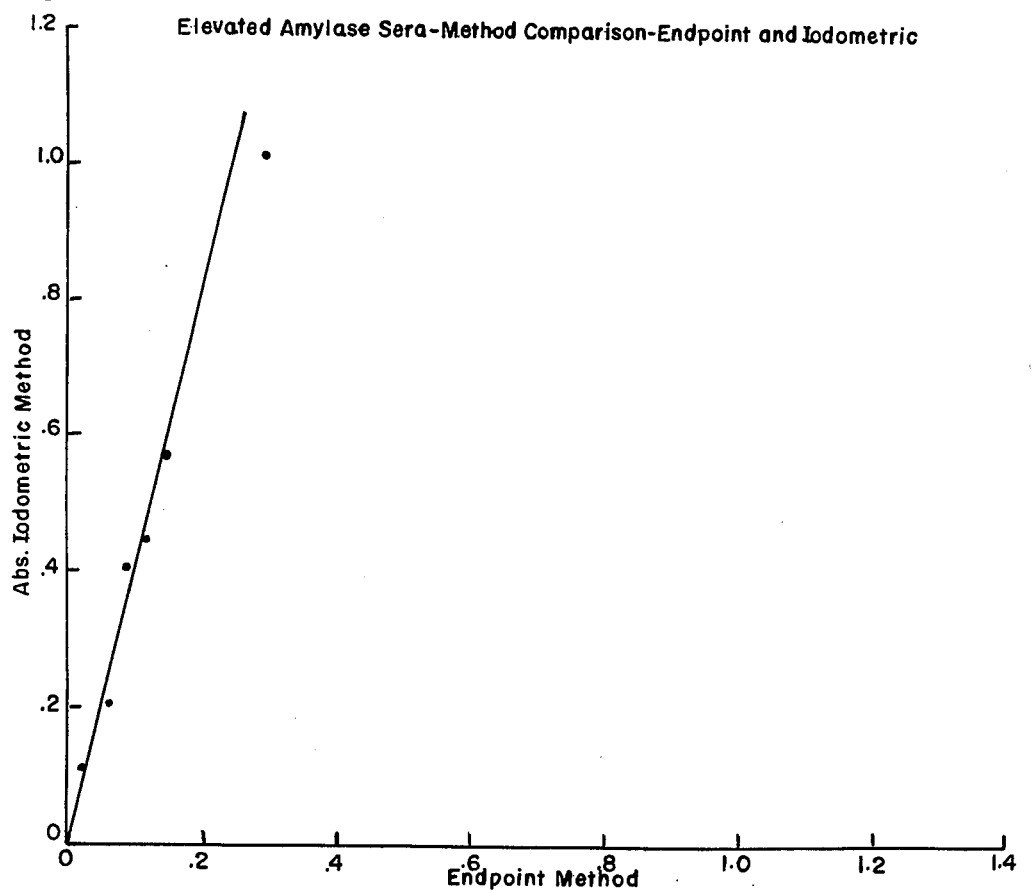

United States Patent [19]

Driscoll et al.

[11] 4,102,747

[45] Jul. 25, 1978

[54] AMYLASE DETERMINATION

[75] Inventors: Richard Cornelius Driscoll, Lake Forest, Ill.; Robert James Gargiulo; Joseph L. Giegel, both of Miami, Fla.

[73] Assignee: American Hospital Supply Corporation, Evanston, Ill.

[21] Appl. No.: 820,072

[22] Filed: Jul. 28, 1977

[51] Int. Cl.$^2$ ............................................. G01N 31/14
[52] U.S. Cl. ................................................ 195/103.5 C
[58] Field of Search .................. 195/103.5 C, 103.5 R, 195/99; 536/45

[56] References Cited

U.S. PATENT DOCUMENTS 3,679,661  7/1972  Babson ..................................... 536/45
3,694,318  9/1972  Klein ....................................... 195/99

OTHER PUBLICATIONS

Bergmeyer "Methods of Enzymatic Analysis", Academic Press, Inc., New York (1972) pp. 885–898.
Janben et al., Nature vol. 182 (1958) pp. 525 & 526.

Primary Examiner—Raymond N. Jones
Assistant Examiner—C. A. Fan
Attorney, Agent, or Firm—Y. Judd Azulay

[57] ABSTRACT

A method for the determination of amylase, based on the cleavage of colorimetric, ultraviolet absorbing or fluorometric substances, commonly referred to as chromogenic substances as p-nitrophenol derivatives of oligosaccharides of chain length 4–10 glucose units. Oligosaccharides of this chain length are resistant to cleavage by $\alpha$ and/or $\beta$-glucosidase and contain endo-$\alpha$-1,4 linkages which are required for amylase activity. Cleavage of the $\alpha$-1,4 bonds by amylase produces smaller fragments which are acted upon by $\alpha$-glucosidase and/or $\beta$-glucosidase to liberate a chromophore. The rate of appearance of the chromophore is proportional to amylase activity and lends itself to either rate or endpoint determinations. The qualitative or quantitative measurement of amylase concentrations in a sample is useful in medical diagnosis.

2 Claims, 2 Drawing Figures

AMYLASE DETERMINATION

SUMMARY OF THE INVENTION

This invention relates to methods of determining amylase activity in biological fluids and more particularly to a novel method for the determination of amylase activity based on the cleavage of chromophore derivatives of oligosaccharides of chain length 4 to 10 glucose units.

BACKGROUND OF THE INVENTION

One of the most widely studied and accepted procedures in clinical chemistry is the determination of serum and urine α-amylase which is used for the diagnosis of pancreatic disease.

During the past twenty-five years various amylase methods have been developed for use in the clinical laboratory. Some of the methods, i.e. saccharogenic method, involves complicated methodology which makes its routine use prohibitive. Other methods, i.e., turbidometric and viscosimetric methods for the determination of α-amylase activity are dependent on changes in the physical properties of the substrate, which may be influenced to a considerable degree by other factors present in the serum. Today, one of the most widely used methods for α-amylase determination is the starch-iodine method. With this method only a specific portion of the substrate is measured and the enzyme does not work under substrate saturation conditions. Further, the presence of serum proteins could interfere with the starch-iodine reaction.

In addition to the above difficulties associated with the mentioned methods, a further difficulty is encountered because the aforementioned methods can be used to determine a rather limited range of α-amylase activity. Also, some of the methods cannot be used for accurate determination of either sub-normal or highly elevated α-amylase levels.

It has been shown that α-amylase activity can be determined based on the solubilization of colored starch grains by α-amylase. It has also been shown that by using cross-linked soluble starch marked with a dye marker under alkaline conditions, α-amylase activity could be determined. However, these reported procedures require elevated incubation temperature, prolonged incubation time and oftentimes double dialysis to achieve adequate sensitivity.

Synthetic fluorogenic and chromogenic starch substrates have also been used to determine amylase activity in biological fluids. In these methods a chromophore is covalently bound to a water insoluble, cross-linked starch. Amylase acts upon the substrate to release water-soluble fragments which are measured spectroscopically after first separating the water-insoluble residue.

In another assay involving a synthetic substrate (Nature, 182 (1958) 525–526) a p-nitrophenol derivative of maltose is used. The p-nitrophenol replaces the anomeric hydroxyl group of maltose. Amylase causes cleavage of the substrate to produce p-nitrophenol which can be monitored at 410 mm. However, the assay is 16 hours long and maltase also cleaves the substrate. In addition, since this derivative has no endo-α-1,4 bond its specificity as an amylase substrate is subject to considerable questions.

The method according to the invention is distinguished from the known prior methods by either greater simplicity, greatly decreased incubation time of greater sensitivity. Further, the method of the present invention is distinguished by using a controlled molecular weight polysaccharide in place of maltose. These controlled molecular weight polysaccharides tagged with p-nitrophenol, while having sufficient chain length to resist cleavage by maltase, and possessing an endo 1,4 bond can still react rapidly with amylase.

BRIEF DESCRIPTION OF THE INVENTION

The invention herein incorporates a new and sensitive method for the determination of serum or α-amylase activity. The new method for the determination of amylase is based on the cleavage of p-nitrophenol derivatives of oligosaccharides of chain length 4 to 10 glucose units. Oligosaccharides of this chain length are resistant to cleavage by α-glucosidase and contain endo-α-1,4 linkages which are required for amylase activity. Cleavage of these α-1,4 bonds by amylase produces smaller fragments which are acted upon by α-glucosidase and/or β-glucosidase to liberate p-nitrophenol. The rate of appearance of p-nitrophenol is thus proportional to amylase activity.

Maltotetraose is the smallest oligosaccharide susceptable to specific cleavage by amylase. Compounds other than p-nitrophenol derivatives could also be used to develop colorimetric, fluorometric and ultraviolet procedures. The p-nitrophenol derivative of an oligosaccharide mixture (of 4 to 10 glucose units) was prepared by acetylation, followed by reaction with p-nitrophenol in the presence of stannic chloride and subsequent deacetylation with sodium methoxide in methanol. The reaction system for determination of amylase consists of the derivativized oligosaccharide, α and β glucosidase, and phosphate buffer. The reaction may be monitored continuously by the change in absorption at 405 nm. Purified hog pancreatic amylase gave linear rates with no lag phase. Preliminary testing with patients' samples gave good correlation with classical amylase methods.

DESCRIPTION OF THE INVENTION

The reaction of the above outlined invention can best be described by reference to the following reaction diagram:

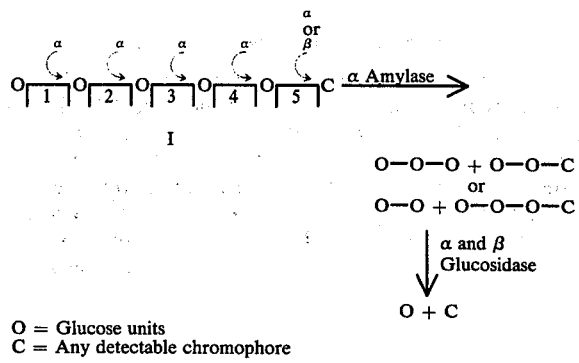

O = Glucose units
C = Any detectable chromophore

α-amylase is known to act preferentially on the endo -1,4 bonds of the polysaccharide molecule such as bonds 2,3 above. α and β glucosidase, on the other hand, prefer exo-bonds such as bonds 1,5 above. However, the α and β glucosidase does not act on carbohydrate molecules longer than 4 glucose units in length. It therefore becomes apparent that a chromophore molecule such as (I) above should be acted upon by amylase at both the 2 and 3 position. The reaction will result in two possible combinations of products depending on the attack point of the amylase, i.e. endo bonds 2 and 3.

To overcome the problems associated with prior amylase procedures, it has been found that controlled molecular weight polysaccharides (4–10 glucose units) can be substituted for maltose. Since amylase acts preferably on endo bonds to form smaller fragments, therefore, $\alpha$ and $\beta$ glucosidase are included in the assay conditions to release the chromophore from the smaller polysaccharide fragments. Specifically, the p-nitrophenol and the 4-methylumbelliferone derivatives, are suitable substrates.

The following examples serve to illustrate a method of preparing the p-nitrophenol substrate required for the inventive method and also the inventive amylase determination method:

EXAMPLE I — SYNTHESIS OF SUBSTRATE a. Acetylation of Oligosaccharide

A suspension of fifty grams of oligosaccharides (DP-5 to DP-10) in 50 ml of pyridine was diluted with 200 ml of acetic anhydride. The mixture was then heated in a water bath (95C) with stirring for 3 hours. While still warm the mixture was poured in 1500 ml of ice water. An oil was formed which eventually solidified with stirring. The solid was washed with water, filtered and dried. Recrystallization of the crude material from 400 ml of ethanol yielded 65 grams of a white solid.

b. Reaction of p-Nitrophenol with Acetylated Oligosaccharides

To a refluxing mixture of 40 grams of acetylated oligosaccharides and 7.5 grams of p-nitrophenol in 120 ml of benzene and 60 ml of chloroform (ethanol free) was added 3 ml of stannic chloride. After refluxing for 15 minutes another 3 ml of stannic chloride was added, followed by 15 minutes of heating. The reaction mixture was then diluted with ethyl acetate (200 ml), and extracted with water and then with saturated sodium bicarbonate to remove the p-nitrophenol. After drying over magnesium sulfate the solvent was removed. The yellow solid can be purified by eluting with ethyl acetate-heptane (4:1) on silica gel. Isolated 13 g of a white solid.

c. Deacetylation of Oligosaccharides

To 7 grams of the p-nitrophenol derivative of the oligosaccharides in 60 ml of methanol and 25 ml of methylene chloride was added 8 ml of a sodium methoxide in methanol solution (prepared from 40 mg of sodium). After 2 days at OC, the white precipitate was isolated by centrifuging the reaction mixture, washed with methanol-methylene chloride (1:1) containing several drops of acetic acid, decanted, and then washed twice with ether. The white solid was dried in vacuo to yield 2 grams of material.

Elemental analysis: Nitrogen 0.64%

EXAMPLE II DETERMINATION OF AMYLASE ACTIVITY a. Endpoint Method

An assay mixture comprising:
1. 0.8 ml Buffer solution (potassium phosphate Buffer $2\times10^{-1}$M containing $5\times10^{-1}$M NaCl and Substrate at concentration of 4 mg/ml Buffer)
2. 0.02 ml $\alpha$ Glucosidase 5 mg/ml
3. 0.02 ml $\beta$ Glucosidase 5 mg/ml
4. 0.05 ml Sample is incubated for exactly 10 minutes at 37° C. After exactly 10 minutes the reaction is stopped by the addition of 3.0 ml of 0.1 N Sodium Hydroxide. The amount of p-nitrophenol released which is proportional to amylase activity is then recorded with time at 405 nm.

FIG. 1 is a comparision graph of elevated Serum Samples from the upper limit of normal to eleven time the upper limit of normal range of 60–150 somogy units/di by a Turbidimetric Method as plotted against the absorbance of each sample as obtained by the endpoint method.

FIG. II shows the absorbances seen with the Endpoint Method as compared with absorbances obtained by the Iodometric Method.

Listed below are the values plotted for Graphs I and II. As can be clearly seen, linear relationships were obtained on both graphs.

| Patient Sample | METHOD COMPARISON DATA in somogy units/di | | | |
|---|---|---|---|---|
| | X Upper Limit of Normal | Turbidimetric Method | Iodometric Method | pnp End Point Method |
| 1 | 1X | 172 | 166 | 192 |
| 2 | 2X | 291 | 300 | 245 |
| 3 | 3X | 421 | 417 | 478 |
| 4 | 4X | 540 | 534 | 528 |
| 5 | 6X | 910 | 858 | 919 |
| 6 | 11X | 1659 | 1717 | 1629 |

What is claimed is:

1. A process for determining the $\alpha$-amylase content of a sample comprising the steps of adding a chromogenic oligosaccharide substrate having 4–10 glucose units and a chromophore selected from the group of p-nitrophenol and 4-methylumbilliferone to a solution containing a measured amount of said sample and $\alpha$ and $\beta$ glucosidase and determining amylase activity by the release of a chromophore selected from the group of p-nitrophenol and 4-methylumbelliferone.

2. The process of claim 1 wherein potassium phosphate is added to the solution as buffer.

* * * * *